(12) United States Patent
Baldwin

(10) Patent No.: US 12,043,226 B2
(45) Date of Patent: Jul. 23, 2024

(54) SHOPPING CART WASHING ASSEMBLY

(71) Applicant: Holly Baldwin, Tyler, TX (US)

(72) Inventor: Holly Baldwin, Tyler, TX (US)

(*) Notice: Subject to any disclaimer, the term of this patent is extended or adjusted under 35 U.S.C. 154(b) by 342 days.

(21) Appl. No.: 17/476,777

(22) Filed: Sep. 16, 2021

(65) Prior Publication Data

US 2023/0079594 A1    Mar. 16, 2023

(51) Int. Cl.
*B60S 3/00*     (2006.01)
*A61L 2/22*     (2006.01)
*A61L 2/18*     (2006.01)

(52) U.S. Cl.
CPC ............... *B60S 3/004* (2013.01); *A61L 2/22* (2013.01); *A61L 2/18* (2013.01); *A61L 2202/122* (2013.01); *A61L 2202/14* (2013.01); *A61L 2202/15* (2013.01); *A61L 2202/16* (2013.01); *A61L 2202/17* (2013.01)

(58) Field of Classification Search
CPC .... B60S 3/004; A61L 2/22; A61L 2/18; A61L 2202/122; A61L 2202/14; A61L 2202/16; A61L 2202/17; A61L 2202/15
See application file for complete search history.

(56) References Cited

U.S. PATENT DOCUMENTS

| | | | | |
|---|---|---|---|---|
| 2,997,048 A | * | 8/1961 | Gertken | B60S 3/004 134/123 |
| 3,179,117 A | * | 4/1965 | Gibson | B60P 3/00 134/107 |
| 3,444,867 A | * | 5/1969 | Thornton | B60S 3/04 134/123 |
| 3,698,029 A | * | 10/1972 | Pulliam | B60S 3/04 134/123 |
| 4,807,319 A | * | 2/1989 | Poitevin | E04H 3/04 134/131 |
| 6,090,218 A | * | 7/2000 | Brackmann | G06Q 30/0238 134/201 |
| 7,258,125 B2 | | 8/2007 | Holbrook | |
| 7,346,956 B2 | | 3/2008 | Andre | |
| 8,381,746 B2 | | 2/2013 | Yoon | |
| 8,480,814 B1 | * | 7/2013 | Fanourgiakis | B08B 3/00 134/29 |
| D802,859 S | | 11/2017 | Lambert | |
| 10,023,156 B2 | | 7/2018 | Serrurier | |
| 10,894,106 B1 | * | 1/2021 | Lopez | A61L 2/20 |
| 2005/0214159 A1 | * | 9/2005 | Schwei | A61L 2/24 422/28 |

(Continued)

FOREIGN PATENT DOCUMENTS

| | | | | |
|---|---|---|---|---|
| CA | 2453869 C | * | 5/2006 | ............. A47F 10/02 |
| EP | 3546076 | | 10/2019 | |

*Primary Examiner* — Benjamin L Osterhout

(57) ABSTRACT

A shopping cart washing assembly includes a tunnel that is positionable in a location which employs shopping carts wherein the tunnel is configured to have the shopping carts moved through the tunnel. A plurality of lower spray nozzles and a plurality of upper spray nozzles is each integrated into the tunnel to spray a liquid for washing shopping carts. A first drive unit and a second drive unit is each movably integrated into the tunnel. A plurality of grappling units each extends between the first drive unit and the second drive unit. Each of the grapping units engages a handle of a respective shopping cart to transport the respective shopping cart through the tunnel.

9 Claims, 3 Drawing Sheets

(56) References Cited

U.S. PATENT DOCUMENTS

| | | | |
|---|---|---|---|
| 2006/0011220 A1* | 1/2006 | Mueller | B08B 3/022 |
| | | | 134/123 |
| 2007/0012340 A1* | 1/2007 | Jones | A61L 2/10 |
| | | | 134/131 |
| 2007/0017548 A1* | 1/2007 | King | A61L 2/24 |
| | | | 134/1 |
| 2008/0029133 A1* | 2/2008 | Kunkle | A61L 2/22 |
| | | | 134/123 |
| 2008/0178412 A1* | 7/2008 | Kiter | A61L 2/10 |
| | | | 15/4 |
| 2008/0210268 A1* | 9/2008 | Metheny | B08B 3/022 |
| | | | 134/95.2 |
| 2008/0289649 A1* | 11/2008 | Woytkiw | B60S 3/00 |
| | | | 134/1 |
| 2009/0050174 A1* | 2/2009 | Gheparde | B08B 7/0071 |
| | | | 134/1 |
| 2010/0122717 A1* | 5/2010 | Yoon | A61L 2/22 |
| | | | 134/137 |
| 2021/0362690 A1* | 11/2021 | Middleton | B60S 3/04 |
| 2021/0386893 A1* | 12/2021 | Lee | A61L 2/26 |
| 2022/0126794 A1* | 4/2022 | Atkins | B60S 3/04 |
| 2022/0133926 A1* | 5/2022 | Gardiner | A61L 2/22 |
| | | | 422/24 |
| 2022/0193288 A1* | 6/2022 | Fanourgiakis | B60S 3/04 |
| 2022/0194329 A1* | 6/2022 | Krull | A61L 2/22 |

* cited by examiner

SHOPPING CART WASHING ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to washing devices and more particularly pertains to a new washing device for automatically washing shopping carts. The device includes a tunnel with a pair of drive belts extending through the tunnel. A plurality of grappling units is coupled between the drive belts and each of the grappling units engages a handle of a shopping cart. A plurality of sprayers is integrated into the tunnel for washing the shopping carts as the shopping carts are transported through the tunnel.

(2) Description of Related Art Including Information Disclosed Under 37 CFR 1.97 and 1.98

The prior art relates to washing devices including a variety of automated shopping cart washing devices that include a tunnel and a plurality of sprayers integrated into the tunnel for automatically washing shopping carts. The prior art discloses a variety of automated washing devices that includes a transporting unit for transporting an object through an elongated washing area.

BRIEF SUMMARY OF THE INVENTION

An embodiment of the disclosure meets the needs presented above by generally comprising a tunnel that is positionable in a location which employs shopping carts wherein the tunnel is configured to have the shopping carts moved through the tunnel. A plurality of lower spray nozzles and a plurality of upper spray nozzles is each integrated into the tunnel to spray a liquid for washing shopping carts. A first drive unit and a second drive unit is each movably integrated into the tunnel. A plurality of grappling units each extends between the first drive unit and the second drive unit. Each of the grapping units engages a handle of a respective shopping cart to transport the respective shopping cart through the tunnel.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
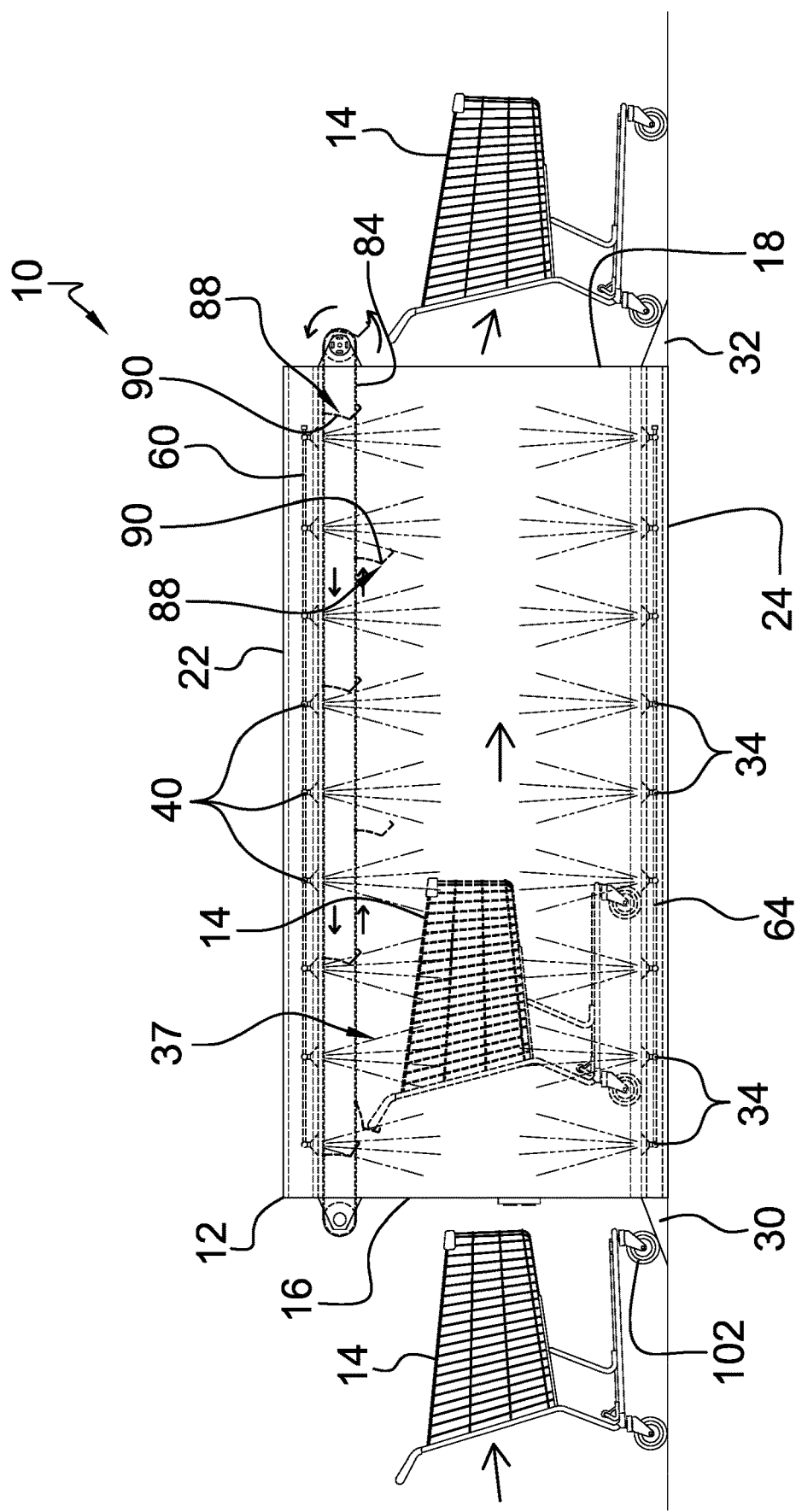
FIG. 1 is a right side phantom view of a shopping cart washing assembly according to an embodiment of the disclosure.
Figure 2:
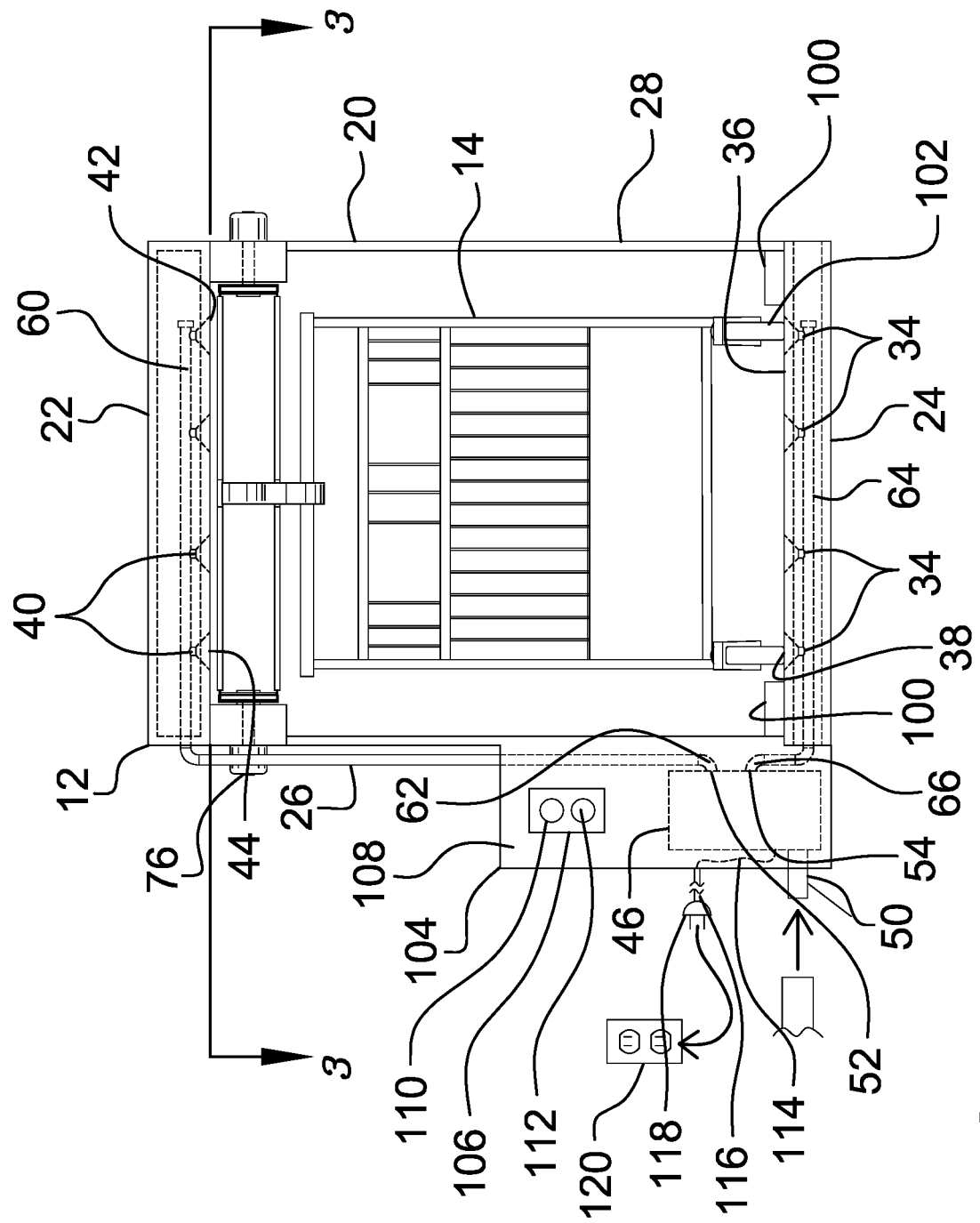
FIG. 2 is a back phantom view of an embodiment of the disclosure.
Figure 3:
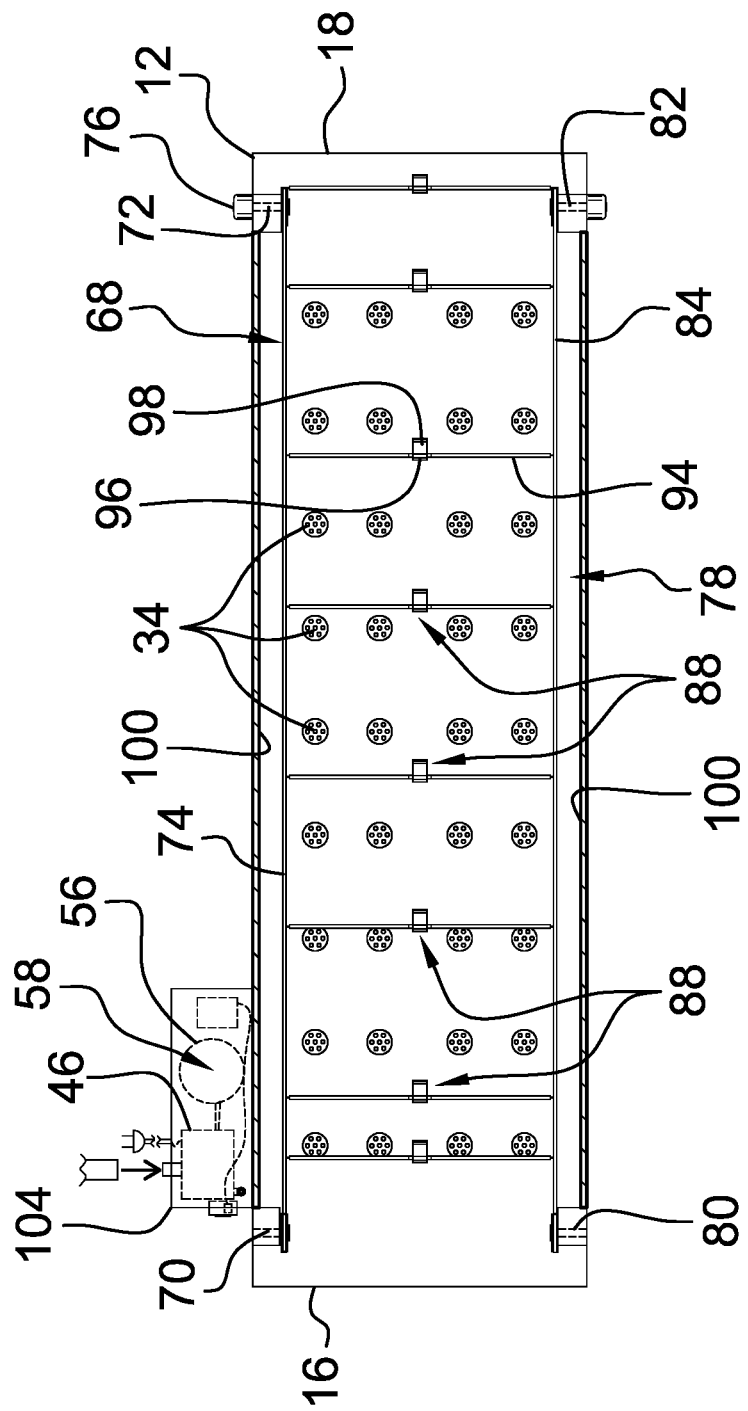
FIG. 3 is a cross sectional view taken along line 3-3 of FIG. 2 of an embodiment of the disclosure.

With reference now to the drawings, and in particular to FIGS. 1 through 3 thereof, a new washing device embodying the principles and concepts of an embodiment of the disclosure and generally designated by the reference numeral 10 will be described.

As best illustrated in FIGS. 1 through 3, the shopping cart washing assembly 10 generally comprises a tunnel 12 that is positionable in a location which employs shopping carts 14 for having the shopping carts 14 being moved through the tunnel 12. The tunnel 12 has a first end 16, a second end 18 and an outer wall 20 extending between the first end 16 and the second end 18. Each of the first end 16 and the second end 18 is open, and the outer wall 20 has a top side 22, a bottom side 24, a first lateral side 26 and a second lateral side 28. A first ramp 30 is positioned against the first end 16 of the tunnel 12 and the first ramp 30 slopes upwardly into the bottom side 24 of the outer wall 20 of the tunnel 12 to facilitate the shopping carts 14 to roll into the tunnel 12. A second ramp 32 is positioned against the second end 18 of the tunnel 12 and the second ramp 32 slopes upwardly into the bottom side 24 of the outer wall 20 of the tunnel 12 to facilitate the shopping carts 14 to roll out, of the tunnel 12.

A plurality of lower spray nozzles 34 is each integrated into a floor 36 of the tunnel 12 to spray a fluid 37 upwardly from the floor 36 for washing shopping carts 14 when the shopping carts 14 are inside of the tunnel 12. Each of the lower spray nozzles 34 is embedded into the bottom side 24 of the outer wall 20, and the lower spray nozzles 34 are spaced apart from each other and are distributed between the first end 16 and the second end 18. The lower spray nozzles 34 are arranged into a plurality of rows that are distributed between the first lateral side 26 and the second lateral side 28 of the outer wall 20 of the tunnel 12. Each of the lower spray nozzles 34 has an open end 38 that is exposed with respect to the bottom side 24 of the outer wall 20. Additionally, the open end 38 is open to spray the fluid 37 upwardly from the bottom side 24 of the outer wall 20.

A plurality of upper spray nozzles 40 is provided and each of the upper spray, nozzles 40 is integrated into a ceiling 42 of the tunnel 12 to spray a fluid 37 downwardly from the ceiling 42 for washing shopping carts 14 when the shopping carts 14 are inside of the tunnel 12. Each of the upper spray nozzles 40 is embedded into the top side 22 of the outer wall 20. Additionally, the upper spray nozzles 40 are spaced apart from each other and are distributed between the first end 16 and the second end 18. The upper spray nozzles 40 are arranged into a plurality of rows that are distributed between the first lateral side 26 and the second lateral side 28 of the outer wall 20 of the tunnel 12. Mach of the upper spray nozzles 40 has an open end 44 that is exposed with respect to the top side 22 of the outer wall 20. The open end 44 of each of the upper spray nozzles 40 is open to spray the fluid 37 downwardly from the top side 22 of the outer wall 20.

A pump 46 is provided and the pump 46 is coupled to the tunnel 12. The pump 46 is in fluid communication with each of the lower spray nozzles 34 and each of the upper spray nozzles 40. Additionally, the pump 46 is in fluid communication with a fluid source 48 to pump 46 the fluid 37 outwardly through each of the upper spray nozzles 40 and each of the lower spray nozzles 34 for washing the shopping carts 14. The pump 46 has an input 50, an upper output 52 and a lower output 54, and the pump 46 may comprise an electric fluid pump or the like with an operational pressure similar to that of a power washer. The fluid source 48 may be a water hose for supplying water to the pump 46. Additionally, a sanitizer reservoir 56 may be provided that contains a fluid sanitizer 58. The sanitizer reservoir 56 may be fluidly coupled to the input 50 of the pump 46 for delivering the fluid sanitizer 58 to the pump 46.

A plurality of upper conduits 60 is provided and each of the upper conduits 60 is fluidly coupled to a respective one of the upper spray nozzles 40. The plurality of upper conduits 60 has a common inlet 62 and the common inlet 62 is fluidly coupled to the upper output 52 of the pump 46. In this way the upper conduits 60 can direct the fluid 37 to each of the upper spray nozzles 40. A plurality of lower conduits 64 is each fluidly coupled to a respective one of the lower spray nozzles 34. The plurality of lower conduits 64 has a common inlet 66 and the common inlet 66 of the lower conduits 64 is fluidly coupled to the lower output 54 of the pump 46 to direct the fluid 37 to each of the lower spray nozzles 34.

A first drive unit 68 is movably integrated into the tunnel 12 and the first drive unit 68 extends along a full length of the tunnel 12. The first drive unit 68 moves in a first direction when the first drive unit 68 is turned on. The first drive unit 68 comprises a first roller 70 that is rotatably positioned on the first end 16 of the tunnel 12, The first roller 70 is positioned adjacent to an intersection between the top side 22 and the first lateral side 26 of the outer wall 20 of the tunnel 12. The first drive unit 68 includes a second roller 72 that is rotatably positioned on the second end 18 of the tunnel 12. The second roller 72 is positioned adjacent to an intersection between the top side 22 and the first lateral side 26 of the outer wall 20 of the tunnel 12.

The first drive unit 68 includes a first belt 74 that extends around each of the first roller 70 and the second roller 72. Additionally, the first drive unit 68 includes a first motor 76 that is coupled to the first roller 70. The first motor 76 rotates the first roller 70 in a first direction when the first motor 76 is turned on. The first motor 76 may comprise an electric motor or the like.

A second drive unit 78 is movably integrated into the tunnel 12 and the second drive unit 78 extends along a full length of the tunnel 12. The second drive unit 78 moves in a first direction when the second drive unit 78 is turned on. The second drive unit 78 comprises a primary roller 80 that is rotatably positioned on the first end 16 of the tunnel 12. The primary roller 80 is positioned adjacent to an intersection between the top side 22 and the second lateral side 28 of the outer wall 20 of the tunnel 12. The second drive unit 78 includes a secondary roller 82 that is rotatably positioned on the second end 18 of the tunnel 12. The secondary roller 82 is positioned adjacent to an intersection between the top side 22 and the second lateral side 28 of the outer wall 20 of the tunnel 12.

The second drive unit 78 includes a second belt 84 that extends around each of the primary roller 80 and the secondary roller 82. The second drive unit 78 includes a second motor 86 that is coupled to the secondary roller 82. Additionally, the second motor 86 rotates the secondary roller 82 in a first direction when the second motor 86 is turned on. The second motor 86 may comprise an electric motor or the like.

A plurality of grappling units 88 is provided and each of the grappling units 88 extends between the first drive unit 68 and the second drive unit 78. Each of the grappling units 88 has an engagement 90 extending downwardly to engage a handle 92 of a respective shopping cart 14. Additionally, each of the grappling units 88 is transported along the tunnel 12 when the first drive unit 68 and the second drive unit 78 are turned on. In this way each of the grappling units 88 can transport the respective shopping cart 14 through the tunnel 12. The grappling units 88 are spaced apart from each other and are distributed along a full length of the first drive unit 68 and the second drive unit 78.

Each of the grappling units 88 comprises a member 94 which extends between the first belt 74 and the second belt 84. The member 94 is comprised of a flexible material such as plastic, rubber or other similar material. Each of the grappling units 88 includes a hook 96 that is coupled to and extends downwardly from the member 94. The hook 96 has a distal end 98 with respect to the member 94 and the hook 96 is curved adjacent to the distal end 98 such that the distal end 98 is directed upwardly such that the hook 96 defines the engagement 90. Moreover, the hook 96 is oriented such that the distal end 98 is directed toward the second end 18 of the tunnel 12. A pair of guides 100 is positioned on the bottom side 24 of the outer wall 20 of the tunnel 12 and each of the guides 100 extends between the first end 16 and the second end 18 of the tunnel 12. Each of the guides 100 is positioned adjacent to a respective one of the first lateral side 26 and the second lateral side 28 of the outer wall 20 to guide wheels 102 on the shopping carts 14 when the shopping carts 14 are transported through the tunnel 12.

A pump housing 104 is coupled to the outer wall 20 of the tunnel 12, and the pump 46 is positioned inside of the pump housing 104. A control panel 106 is coupled to an outside wall 108 of the pump housing 104 such that the control panel 106 is accessible to a user. The control panel 106 is in electrical communication with each of the first drive unit 68, the second drive unit 78 and the pump 46. Additionally, the control panel 106 controls operational parameters of each of the first drive unit 68, the second drive unit 78 and the pump 46.

The control panel 106 includes an on button 110 and an off button 112. The on button 110 turns on each of the first drive unit 68, the second drive unit 78 and the pump 46 when the on button is depressed. The off button 112 turns off each of the first drive unit 68, the second drive unit 78 and the pump 46 when the off button 112 is depressed. A power cord 114 is coupled to and extends away from the control panel 106 and the power cord 114 is electrically coupled to the control panel 106. The power cord 114 has a distal end 116 with respect to the control panel 106 and a male plug 118 is electrically coupled to this distal end 116 that can be plugged into a female electrical outlet 120.

In use, the on button 110 on the control panel 106 is depressed and the shopping carts 14 are fed into the first end 16 of the tunnel 12 such that each of the grappling units 88 can engage the handle 92 of a respective shopping cart 14. In this way the shopping carts 14 are transported through the tunnel 12. Each of the upper spray nozzles 40 and the lower spray nozzles 34 washes the shopping carts 14 as they are transported through the tunnel 12. In this way the shopping carts 14 are automatically washed. Additionally, the shopping carts 14 can be automatically sanitized when the fluid sanitizer 58 is supplied to the pump 46.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A shopping cart washing assembly for automatically washing shopping carts, said assembly comprising:
   a tunnel being positionable in a location which employs shopping carts wherein said tunnel is configured to have the shopping carts moved through said tunnel;
   a plurality of lower spray nozzles, each of said lower spray nozzles being integrated into a floor of said tunnel wherein each of said lower spray nozzles is configured to spray a liquid upwardly from said floor for washing shopping carts when the shopping carts are inside of said tunnel;
   a plurality of upper spray nozzles, each of said upper spray nozzles being integrated into a ceiling of said tunnel wherein each of said upper spray nozzles is configured to spray a liquid downwardly from said ceiling for washing shopping carts when the shopping carts are inside of said tunnel;
   a pump being coupled to said tunnel, said pump being in fluid communication with each of said lower spray nozzles and each of said upper spray nozzles, said pump being in fluid communication with a fluid source wherein said pump is configured to pump the fluid outwardly through each of said upper spray nozzles and each of said lower spray nozzles for washing the shopping carts;
   a first drive unit being movably integrated into said tunnel, said first drive unit extending along a full length of said tunnel, said first drive unit moving in a first direction when said first drive unit is turned on;
   a second drive unit being movably integrated into said tunnel, said second drive unit extending along a full length of said tunnel, said second drive unit moving in the first direction when said second drive unit is turned on and
   a plurality of grappling units, each of said grappling units extending between said first drive unit and said second drive unit, each of said grappling units having an engagement extending downwardly wherein said engagement of each of said grappling units is configured to engage a handle of a respective shopping cart, each of said qrappling units being transported along said tunnel when said first drive unit and said second drive unit are turned on wherein each of said grappling units is configured to transport the respective shopping cart through said tunnel.

2. The assembly according to claim 1, further comprising:
   a pump housing being coupled to an outer wall of said tunnel, said pump being positioned inside of said pump housing;
   a control panel being coupled to an outside wall of said pump housing wherein said control panel is configured to be accessible to a user said control panel being in electrical communication with each of said first drive unit, said second drive unit and said pump, said control panel controlling operation of each of said first drive unit, said second drive unit and said pump, said control panel including an on button and an off button, said on button turning on each of said first drive unit, said second drive unit and said pump when said on button is depressed, said off button turning off each of said first drive unit, said second drive unit and said pump when said off button is depressed; and
   a power cord being coupled to and extending away from said control panel, said power cord being electrically coupled to said control panel, said power cord having a distal end with respect to said control panel, said distal end having a male plug being electrically coupled thereto wherein said male plug is configured to be plugged into a female electrical outlet.

3. The assembly according to claim 1, wherein:
   said tunnel has a first end, a second end and an outer will extending between said first end and said second end, each of said first end and said second end being open, said outer wall having a top side, a bottom side, a first lateral side and a second lateral side;
   said assembly includes a first ramp being positioned against said first end of said tunnel, said first ramp sloping upwardly into said bottom side of said outer wall of said tunnel wherein said first ramp is configured to facilitate the shopping carts to roll into said tunnel;
   said assembly includes a second ramp being positioned against said second end of said tunnel, said second ramp sloping upwardly into said bottom side of said outer wall of said tunnel wherein said second ramp is configured to facilitate the shopping carts to roll out of said tunnel;

each of said lower spray nozzles is embedded into said bottom side of said outer wall, said lower spray nozzles being spaced apart from each other and being distributed between said first end and said second end, said lower spray nozzles being arranged into a plurality of rows being distributed between said first lateral side and said second lateral side of said outer wall of said tunnel, each of said lower spray nozzles having an open end being exposed with respect to said bottom side of said outer wall, said open end being open wherein said open end is configured to spray the fluid upwardly from said bottom side of said outer wall; and each of said upper spray nozzles is embedded into said top side of said outer wall, said upper spray nozzles being spaced apart from each other and being distributed between said first end and said second end, said upper spray, nozzles being arranged into a plurality of rows being distributed between said first, lateral side and said second lateral side of said outer wall of said tunnel, each of said upper spray nozzles having an open end being exposed with respect to said top side of said outer wall, said open end of each of said upper spray nozzles being open wherein said open end of each of said upper spray nozzles is configured to spray the fluid downwardly from said top side of said outer wall.

4. The assembly according to claim 3, further comprising a pair of guides, each of said guides being positioned on said bottom side of said outer wall of said tunnel, each of said guides extending between said first end and said second end of said tunnel, each of said guides being positioned adjacent to a respective one of said first lateral side and said second lateral side of said outer wall wherein each of said guides is configured to guide wheels on the shopping carts when the shopping carts are transported through said tunnel.

5. The assembly according to claim 3, wherein:
said pump has an input, and an upper output and a lower output;
said assembly includes a plurality of upper conduits, each of said upper conduits being fluidly coupled to a respective one of said upper nozzles, said plurality of upper conduits having a common inlet, said common inlet being fluidly coupled to said upper output of said pump wherein said upper conduits are configured to direct the fluid to each of said upper spray nozzles; and
said assembly includes a plurality of lower conduits, each of said lower conduits being fluidly coupled to a respective one of said lower nozzles, said plurality of lower conduits having a common inlet, said common inlet of said lower conduits being fluidly coupled to said lower output of said pump wherein said lower conduits are configured to direct the fluid to each of said lower spray nozzles.

6. The assembly according to claim 3, wherein said first drive unit comprises:
a first roller being rotatably positioned on said first end of said tunnel, said first roller being positioned adjacent, to an intersection between said top side and said first lateral side of said outer wall of said tunnel;
a second roller being rotatably positioned on said second end of said tunnel, said second roller being positioned adjacent to an intersection between said top side and said first lateral side of said outer wall of said tunnel:
a first belt extending around each of said first roller and said second roller; and
a first motor being coupled to said first roller such that said first motor rotates said first roller in the first direction when said first motor is turned on.

7. The assembly according to claim 6, wherein said second drive unit comprises:
a primary roller being rotatably positioned on said first end of said tunnel, said primary roller being positioned adjacent to an intersection between said top side and said second lateral side of said outer wall of said tunnel;
a secondary roller being rotatably positioned on said second end of said tunnel, said secondary roller being positioned adjacent to an intersection between said top side and said second lateral side of said outer wall of said tunnel;
a second belt extending around each of said primary roller and said secondary roller; and
a second motor being coupled to said secondary roller such that said second motor rotates said secondary roller in the first direction when said second motor is turned on.

8. The assembly according to claim 7, wherein each of said grappling units comprises:
a member extending between said first belt and said second belt; and
a hook being coupled to and extending downwardly from said member, said hook having a distal end with respect to said member, said hook being curved adjacent to said distal end such that said distal end is directed upwardly wherein said hook defines said engagement, said hook being oriented such that said distal end is directed toward said second end of said tunnel.

9. A shopping cart washing assembly for automatically washing shopping carts, said assembly comprising:
a tunnel being positionable in a location which employs shopping carts wherein said tunnel is configured to have the shopping carts moved through said tunnel, said tunnel having a first end, a second end and an outer wall extending between said first end and said second end, each of said first end and said second end being open, said outer wall having a top side, a bottom side, a first lateral side and a second lateral side;
a first, limp being positioned against said first end of said tunnel, said first ramp sloping upwardly into said bottom side of said outer wall of said tunnel wherein said first ramp is configured to facilitate the shopping carts to roll into said tunnel;
a second ramp being positioned against said second end of said tunnel, said second ramp sloping upwardly into said bottom side of said outer wall of said tunnel wherein said second ramp is configured to facilitate the shopping carts to roll out of said tunnel;
a plurality of lower spray nozzles, each of said lower spray nozzles being integrated into a floor of said tunnel wherein each of said lower spray nozzles is configured to spray a liquid upwardly from said floor for washing shopping carts when the shopping carts are inside of said tunnel, each of said lower spray nozzles being embedded into said bottom side of said outer wall, said lower spray nozzles being spaced apart from each other and being distributed between said first end and said second end, said lower spray nozzles being arranged into a plurality of rows being distributed between said first lateral side and said second lateral side of said outer wall of said tunnel, each of said lower spray nozzles having an open end being exposed with respect to said bottom side of said outer wall, said open end being open wherein said open end is configured to spray the fluid upwardly from said bottom side of said outer wall;

a plurality of upper spray nozzles, each of said upper spray nozzles being integrated into a ceiling of said tunnel wherein each of said upper spray nozzles is configured to spray a liquid downwardly from said ceiling for washing shopping carts when the shopping carts are inside of said tunnel, each of said upper spray nozzles being embedded into said top side of said outer wall, said upper spray nozzles being spaced apart from each other and being distributed between said first end and said second end, said upper spray nozzles being arranged into a plurality of rows being distributed between said first lateral side and said second lateral side of said outer wall of said tunnel, each of said upper spray nozzles having an open end being exposed with respect to said top side of said outer wall, said open end of each of said upper spray nozzles being open wherein said open end of each of said upper spray nozzles is configured to spray the fluid downwardly from said top side of said outer wall;

a pump being coupled to said tunnel, said pump being in fluid communication with each of said lower spray nozzles and each of said upper spray nozzles, said pump being in fluid communication with a fluid source wherein said pump is configured to pump the fluid outwardly through each of said upper spray nozzles and each of said lower spray nozzles for washing the shopping carts, said pump having an input, and an upper output and a lower output;

a plurality of upper conduits, each of said upper conduits being fluidly coupled to a respective one of said upper nozzles, said plurality of upper conduits having a common inlet, said common inlet being fluidly coupled to said upper output of said pump wherein said upper conduits are configured to direct the fluid to each of said upper spray nozzles;

plurality of lower conduits, each of said lower conduits being fluidly coupled to a respective one of said lower nozzles, said plurality of lower conduits having a common inlet, said common inlet of said lower conduits being fluidly coupled to said lower output of said pump wherein said lower conduits are configured to direct the fluid to each of said lower spray nozzles;

a first drive unit being movably integrated into said tunnel, said first drive unit extending along a full length of said tunnel, said first drive unit moving in a first direction when said first drive unit is turned on, said first drive unit comprising:
 a first roller being rotatably positioned on said first end of said tunnel, said first roller being positioned adjacent to an intersection between said top side and said first lateral side of said outer wall of said tunnel;
 a second roller being rotatably positioned on said second end of said tunnel, said second roller being positioned adjacent to an intersection between said top side and said second lateral side of said outer wall of said tunnel;
 a first belt extending around each of said first roller and said second roller; and
 a first motor being coupled to said first roller such that said first motor rotates said first roller in the first direction when said first motor is turned on;

a second drive unit being movably integrated into said tunnel, said second drive unit extending along a full length of said tunnel, said second drive unit moving in the first direction when said second drive, unit is turned on, said second drive unit comprising:
 a primary roller being rotatably positioned on said first end of said tunnel, said primary roller being positioned adjacent to an intersection between said top side and said second lateral side of said outer wall of said tunnel;
 a secondary roller being rotatably positioned on said second end of said tunnel, said secondary roller being positioned adjacent to an intersection between said top side and said second lateral side of said outer wall of said tunnel;
 a second belt extending around each of said primary roller and said secondary roller; and
 a second motor being coupled to said secondary roller such that said second motor rotates said secondary roller in the first direction when said second motor is turned on;

a plurality of grappling units, each of said grappling units extending between said first drive unit and said second drive unit, each of said grappling units having an engagement extending downwardly wherein said engagement of each of said grappling units is configured to engage a handle of a respective shopping cart, each of said grappling units being transported along said tunnel when said first drive unit and said second drive unit are turned on wherein each of said grappling units is configured to transport the respective shopping cart through said tunnel, each of said grappling units comprising:
 a member extending between said first belt and said second belt; and
 a hook being coupled to and extending downwardly from said member, said hook having a distal end with respect to said member, said hook being curved adjacent, to said distal end such that said distal end is directed upwardly wherein said hook defines said engagement, said hook being oriented such that said distal end is directed toward said second end of said tunnel;

a pair of guides, each of said guides being positioned on said bottom side of said outer wall of said tunnel, each of said guides extending between said first end and said second end of said tunnel, each of said guides being positioned adjacent to a respective one of said first lateral side and said second lateral side of said outer wall wherein each of said guides is configured to guide wheels on the shopping carts when the shopping carts are transported through said tunnel;

a pump housing being coupled to said outer wall of said tunnel, said pump being positioned inside of said pump housing;

a control panel being coupled to an outside wall of said pump housing wherein said control panel is configured to be accessible to a user, said control panel being in electrical communication with each of said first drive unit, said second drive unit and said pump, said control panel controlling operation of each of said first drive unit, said second drive unit and said pump, said control panel including an on button and an off button, said on button turning on each of said first drive unit, said second drive unit and said pump when said on button is depressed, said off button turning off each of said first drive unit, said second drive unit and said pump when said off button is depressed; and a power cord being coupled to and extending away from said control panel, said power cord being electrically coupled to said control panel, said power cord having a distal end with respect to said control panel, said distal end having a male plug being electrically coupled thereto wherein said male plug is configured to be plugged into a female electrical outlet.

\* \* \* \* \*